United States Patent
Spence et al.

(10) Patent No.: US 10,716,908 B2
(45) Date of Patent: Jul. 21, 2020

(54) INFANT CPAP DEVICE, INTERFACE AND SYSTEM

(71) Applicant: Fisher & Paykel Healthcare Limited, Auckland (NZ)

(72) Inventors: Callum James Thomas Spence, Auckland (NZ); Rachael Porter, Auckland (NZ); Craig Karl White, Auckland (NZ); Alicia Jerram Hunter Evans, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1066 days.

(21) Appl. No.: 14/910,231

(22) PCT Filed: Aug. 6, 2014

(86) PCT No.: PCT/NZ2014/000161
§ 371 (c)(1),
(2) Date: Feb. 4, 2016

(87) PCT Pub. No.: WO2015/020538
PCT Pub. Date: Feb. 12, 2015

(65) Prior Publication Data
US 2016/0175548 A1   Jun. 23, 2016

Related U.S. Application Data

(60) Provisional application No. 61/862,883, filed on Aug. 6, 2013.

(51) Int. Cl.
*A61M 16/00* (2006.01)
*A61M 16/16* (2006.01)
(Continued)

(52) U.S. Cl.
CPC .... *A61M 16/0057* (2013.01); *A61M 16/0006* (2014.02); *A61M 16/0666* (2013.01);
(Continued)

(58) Field of Classification Search
CPC .......... A61M 16/0057; A61M 16/0006; A61M 16/0672; A61M 16/125; A61M 16/0666;
(Continued)

(56) References Cited

U.S. PATENT DOCUMENTS

2003/0079749 A1*   5/2003   Strickland ......... A61M 16/0666
                                              128/203.22
2005/0121037 A1*   6/2005   Wood ................ A61M 16/0666
                                              128/207.18
(Continued)

FOREIGN PATENT DOCUMENTS

EP         0549299 A2       6/1993
WO    WO2004/073778 A1      9/2004
(Continued)

OTHER PUBLICATIONS

International Search Report and Written Opinion; dated Dec. 8, 2014; PCT/NZ2014/000161.

*Primary Examiner* — Timothy A Stanis
*Assistant Examiner* — Jonathan S Paciorek
(74) *Attorney, Agent, or Firm* — Knobbe, Martens, Olson & Bear, LLP

(57) ABSTRACT

An infant positive airway pressure (PAP) or continuous positive airway pressure (CPAP) device and related patient interface and system, which can provide a flow of breathing gas to the patient interface. The device can be incorporated into the patient interface and includes at least one interior passage in the shape of a nozzle having a throat, a first portion upstream of the throat and a second portion downstream of the throat relative to the flow of breathing gas. The (Continued)

passage has a vent opening within the second portion and the interior passage defines a continuously curved surface extending between the throat and the vent opening. The second portion of the nozzle preferably is divergent and the first portion can be convergent or non-convergent (e.g., constant cross-section).

23 Claims, 12 Drawing Sheets

(51) Int. Cl.
*A61M 16/06* (2006.01)
*A61M 16/12* (2006.01)
*A61M 16/08* (2006.01)
*A61M 16/10* (2006.01)

(52) U.S. Cl.
CPC .... *A61M 16/0672* (2014.02); *A61M 16/0816* (2013.01); *A61M 16/125* (2014.02); *A61M 16/16* (2013.01); *A61M 16/0683* (2013.01); *A61M 16/1095* (2014.02); *A61M 2205/3368* (2013.01); *A61M 2206/10* (2013.01); *A61M 2240/00* (2013.01)

(58) Field of Classification Search
CPC .............. A61M 16/0816; A61M 16/16; A61M 16/1095; A61M 16/0683; A61M 2205/3368; A61M 2206/10; A61M 2240/00
See application file for complete search history.

(56) References Cited

U.S. PATENT DOCUMENTS

| | | | | |
|---|---|---|---|---|
| 2005/0133039 | A1* | 6/2005 | Wood | A61M 16/0666 128/207.18 |
| 2009/0299158 | A1* | 12/2009 | Boatner | A61B 5/01 600/301 |
| 2011/0214676 | A1* | 9/2011 | Allum | A61M 16/00 128/207.18 |

FOREIGN PATENT DOCUMENTS

| | | |
|---|---|---|
| WO | WO 2007/053878 A1 | 5/2007 |
| WO | WO 2007/064660 A2 | 6/2007 |
| WO | WO 2011/059346 A1 | 5/2011 |

* cited by examiner

INFANT CPAP DEVICE, INTERFACE AND SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The present invention relates to breathing assistance systems and methods. In particular, the present invention relates to systems and methods for providing positive airway pressure therapy to a patient, such as an infant patient.

BACKGROUND ART

Under certain circumstances it is necessary or desirable to provide breathing assistance to a patient under respiratory distress. For example, breathing assistance is often a necessary therapy to treat respiratory distress syndrome (RDS) in infants, which can also be referred to as neonatal respiratory distress syndrome. The breathing assistance provided is often in the form of providing a flow of breathing gas at a positive pressure, or a pressure somewhat greater than atmospheric pressure. Such treatments may be referred to in general as positive airway pressure (PAP) therapy. Often, the positive pressure is provided by a continuous flow of breathing gas, which is referred to as continuous positive airway pressure (CPAP) therapy.

It is therefore an object of the present invention to provide breathing assistance systems and methods and/or systems and methods for providing positive airway pressure therapy to a patient, such as an infant patient, which will go at least some way towards addressing the foregoing problems or which will at least provide the industry/public with a useful choice.

Further aspects and advantages of the present invention will become apparent from the ensuing description which is given by way of example only.

SUMMARY OF THE INVENTION

The systems, methods and devices described herein have innovative aspects, no single one of which is indispensable or solely responsible for their desirable attributes. Without limiting the scope of the claims, some of the advantageous features will now be summarized.

One or more embodiments involve an infant patient nasal respiratory therapy system including a pair of nasal prongs, each configured to create at least a semi-seal with a nare of an infant patient. A first supply tube and a second supply tube each supply a flow of breathing gas to a respective one of the pair of nasal prongs. Each of a pair of connectors connects one of the first and second supply tubes to one of the nasal prongs. Each connector defines an interior passage in the shape of a nozzle having a throat, a first portion between the supply tube and the throat and a second portion between the throat and the nasal prong. The passage comprises a vent opening within the second portion. The interior passage defines a continuously curved surface extending between the throat and the vent opening.

In some configurations, the pair of nasal prongs, the first and second supply tubes and the pair of connectors are separate from one another. The system can further comprise a frame portion that forms a portion of a patient interface and supports at least one of the pair of nasal prongs and the pair of connectors. In some configurations, the vent opening defines a vent opening axis that forms an acute angle with a first axis defined by the first portion.

In some configurations, the second portion is divergent. The first portion can be convergent. The first portion can alternatively define a substantially constant cross-sectional size and shape. In such configurations, the cross-sectional size and shape of the first portion can be substantially identical to a cross-sectional size and shape of the throat.

In some configurations, the first portion defines a first axis and the second portion defines a second axis, wherein the first axis and the second axis are coaxial. The system can include a flow generator that generates the flow of breathing gas. The system can also include a humidifier downstream of the flow generator that humidifies the flow of breathing gas supplied to the first and second supply tubes. In some configurations, at least a bottom section of the second portion is twisted about the second axis.

One or more embodiments involve an infant patient nasal interface for use with a respiratory therapy system that delivers a flow of breathing gas. The interface can include at least one nasal prong configured to be inserted within a nare of an infant patient. A conduit portion is upstream from the nasal prong relative to the flow of breathing gas and defines an interior passage in the shape of a nozzle having a throat, a first portion upstream of the throat and a second portion downstream of the throat. The passage also has a vent opening within the second portion. The interior passage defines a continuously curved surface extending between the throat and the vent opening.

In some configurations, the vent opening defines a vent opening axis that forms an acute angle with a first axis defined by the first portion. The second portion can be divergent. The first portion can be convergent. Alternatively, the first portion can define a substantially constant cross-sectional size and shape. In such configurations, the cross-sectional size and shape of the first portion can be substantially identical to a cross-sectional size and shape of the throat.

In some configurations, the first portion defines a first axis and the second portion defines a second axis, wherein the first axis and the second axis are coaxial. In some configurations, the passage further comprises a pair of opposed transition surface portions between a bottom section of the second portion and a vent portion that defines the vent opening, wherein the transition surface portions create a generally smooth transition between the bottom section of the second portion and the vent portion and are devoid of sharp corners or edges. The transition portions can be either linear or of a concave curvature. In some configurations, at least a bottom section of the second portion is twisted about the second axis.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
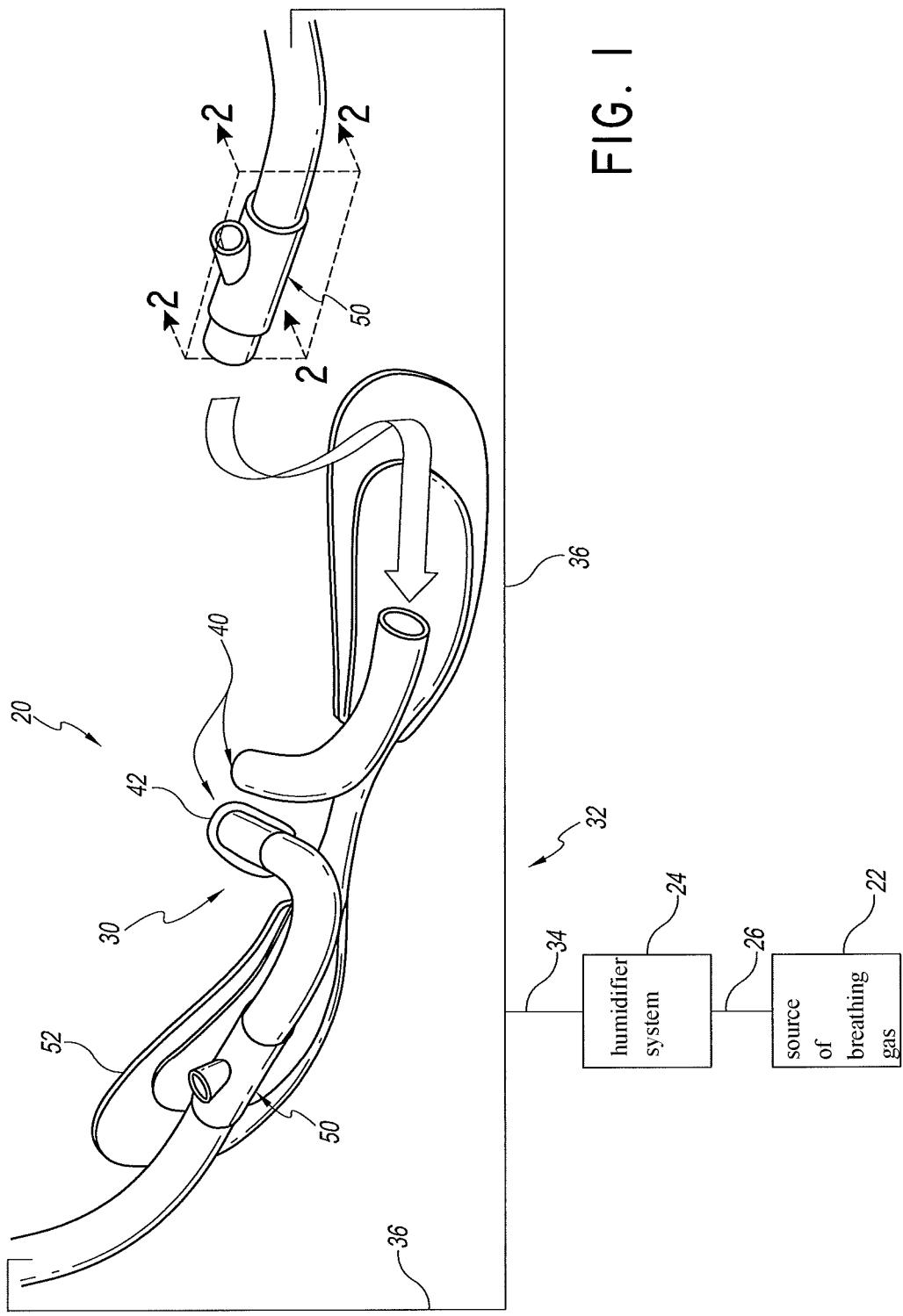
FIG. 1 illustrates a respiratory therapy system including a patient interface comprising a pair of positive airway pressure devices or components having certain features, aspects and advantages of the preferred embodiments.

FIG. 1 illustrates an infant positive airway pressure (PAP) or continuous positive airway pressure (CPAP) system, generally referred to by the reference numeral 20. The system 20 is capable of providing PAP or CPAP therapy to a neonate or an infant patient. In the illustrated arrangement, the therapy is provided nasally and can be referred to as nasal continuous positive airway pressure (nCPAP). In some arrangements, the therapy can be provided through other non-invasive (NIV) interfaces, such as masks. The present system 20 is disclosed herein in the context of continuous positive airway pressure (CPAP) therapy; however, the system 20 could also provide other types or modes of positive airway pressure (PAP) therapy. Accordingly, references to CPAP therapy herein are understood to also include other types of PAP therapies, unless specifically noted otherwise.

Preferably, the system 20 is configured to provide pressure oscillations during at least a portion of a breathing cycle, such as during one or both of the inhalation phase and the exhalation phase of the breathing cycle. It is believed that such pressure oscillations are beneficial to the infant patient and may result in improved gas exchange and reduce the infant patient's work of breathing. A common oscillating pressure expiratory pressure device is a fluid resistance valve, in particular a liquid or water resistance valve, which is often referred to as a bubbler. In the preferred embodiments, the system 20 includes a simpler oscillatory pressure device that is cheaper, smaller and easier to set-up and use compared to a bubbler. In some arrangements, as described herein, the oscillatory pressure device is coupled to or integrated with a patient interface.

In general, the illustrated system 20 includes a source of breathing gas 22, which can be a gas cylinder, a wall supply, a flow generator utilizing ambient air or any other suitable source of breathing gas, or combinations thereof. The breathing gas can be ambient air, oxygen, a blend of air and oxygen, or any other suitable gas for use in respiratory therapy. Preferably, the source of breathing gas 20 provides a flow of breathing gas at a desired flow rate or within a desired range of flow rates. In some arrangements, the flow rate of the flow of breathing gas can be adjusted by a suitable adjuster to a suitable level for the desired therapy.

The flow of breathing gas provided by the source 22 can be delivered to an optional humidifier system 24 by a suitable conduit, such as an inspiratory tube or supply tube 26. The humidifier system 24 provides humidity or vaporized liquid, such as water, to the flow of breathing gas received from the source 22 to output a flow of humidified breathing gas to the patient interface 30 through a suitable conduit 32, which in some arrangements may include a main delivery conduit 34 and one or more supply tubes 36. The humidifier system 24 can include a humidifier unit or humidifier and a humidifier chamber. The humidifier chamber holds a volume of liquid, such as water, which is heated by the humidifier to create a vapor within the humidifier chamber that is transferred to the flow of breathing gas. An example of a suitable humidifier system 24 is the MR850 humidifier and MR225 or MR290 humidifier chamber sold by Fisher & Paykel Healthcare Limited. The humidifier system 24 can output a flow of humidified breathing gas at a desired temperature and absolute humidity, such as an optimal temperature of about 37 degrees Celsius and absolute humidity of about 44 mg/L, or within a desirable or acceptable range of the optimal or desirable temperature and absolute humidity.

All or a portion of the conduit 32 (e.g., the main delivery conduit 34) can be a heated tube such that a temperature of the flow of breathing gas is maintained at an elevated level within the conduit 32 and to avoid or limit condensation within the conduit 32 or patient interface 30. A heater wire can connect a heating element of the conduit 32 to the humidifier system 24 (or other power/heat source) to power the heating element. A sensor or probe can be used to detect the temperature and/or flow rate of the flow of breathing gas through the conduit 32. The humidifier system 24 can utilize information from the sensor to control the operating parameters of the humidifier system 24, for example, to maintain the temperature and/or humidity of the flow of breathing gas within the conduit 32 at a desirable level or within a desirable range.

From the humidifier system 24, the flow of breathing gas is supplied to the patient interface 30, which can be any suitable type of interface capable of supplying a breathing gas to the respiratory system of the patient. The illustrated interface 30 is a nasal interface, which includes at least one and, in some arrangements, a pair of nasal cannula or nasal prongs 40 that are inserted into the nostrils of the infant patient. Preferred interfaces 30 provide a partially, semi-sealed or fully sealed system that delivers the flow of breathing gas to the infant patient and receives expiratory gases from the patient. For example, in some arrangements, each of the nasal prongs 40 can incorporate a seal member 42 (only one shown) that is positioned within the nares of the infant patient and configured to limit or substantially prevent leakage between the prongs 40 and the nares. Such an arrangement assists in maintaining a desirable airway pressure in the patient's anatomy.

Preferably, the system 20 is a flow driven system and, in particular, a biased flow system in which breathing gas is constantly flowing within the system 20 generally in a direction from an inlet of the patient interface 30 toward a patient outlet of the patient interface 30. Thus, the infant patient 12 can inhale a portion of the flow of breathing gas and the remainder is passed through the patient interface 14. Exhaled or expiratory gases can mix with the flow of breathing gas and exit the patient interface 30 along with the unused portion of the flow of breathing gas. For convenience, the gases exiting the patient interface 30 can be referred to as expiratory gases or the flow of breathing gas, although it is understood that either or both of patient-exhaled gases and unused breathing gases can be present at any particular point in time.

As described above, preferably, the system 20, and, in particular, the patient interface 30 includes at least one positive airway pressure device or component 50 that creates or facilitates the creation of a positive airway pressure (PAP) and, preferably, a continuous positive airway pressure (CPAP). In at least some configurations, the component 50 creates or facilitates the creation of pressure fluctuations or oscillations during at least a portion of the breathing cycle.

In the illustrated arrangement, the patient interface 30 comprises a pair of nasal prongs 40, each of which is connected to a supply tube 36. Preferably, one of the components 50 is interposed between each of the supply tubes 36 and the nasal prongs 40. The component 50 can couple the supply tube 36 to the nasal prong 40 and, therefore, can be referred to herein as a CPAP connector 50, or simply a connector 50. In some configurations, one or more of the component 50, the supply tube 36 and the nasal prong 40 can be integrated or unitarily formed. Furthermore, in the illustrated arrangement, each connector 50 and nasal prong 40 are separate from one another. In addition, the supply tubes 36 can also be separate from one another. Preferably, the separate nasal prongs 40 (and, in the illustrated arrangement, the connectors 50) are supported on an interface member or frame 52, which preferably rests against the face of the patient when the patient interface 30 is in use. In some configurations, the system 20 can have a single component 50 that is coupled to both supply tubes 36 (e.g., through a 3-way connector) to be in fluid communication with both nasal prongs 40. The single component 50 can be coupled to a common supply tube that is in fluid communication with a source 22. In some configurations, the nasal prongs 40 can be interconnected and in fluid communication with one other.

Figure 2:
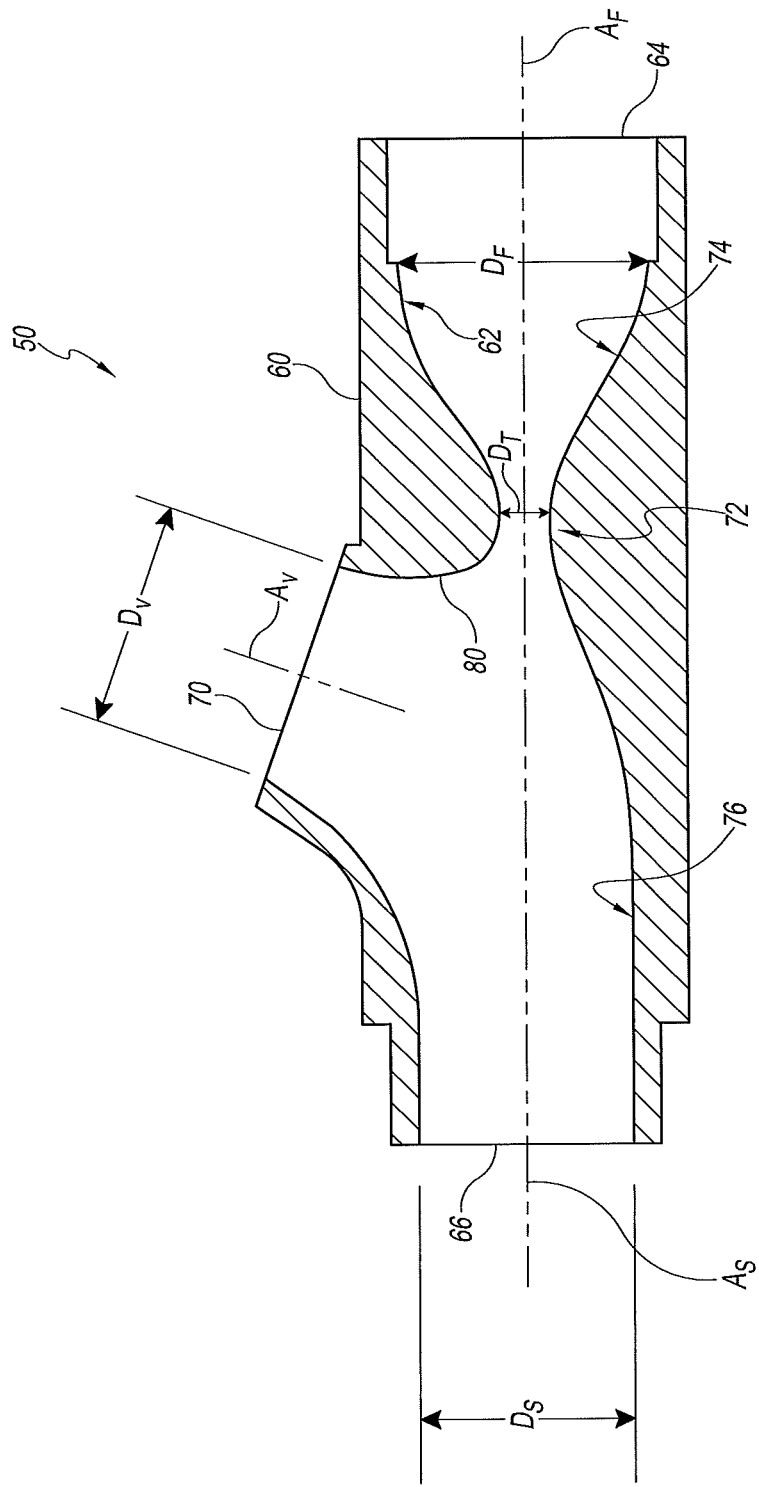
FIG. 2 is a sectional view of one of the positive airway pressure components taken along the line 2-2 of FIG. 1 and illustrating a shape of a passage defined by the component.

With additional reference to FIG. 2, a connector 50 is shown separate from the other components of the patient interface 30. The illustrated connector 50 comprises a body 60, which can be generally cylindrical in shape. The body 60 defines an internal passage 62 having a first end 64 and a second end 66. An optional vent opening or expiratory port 70 communicates with the passage 62 between the first end 64 and the second end 66. The connector 50 is oriented such that the flow of breathing gas provided by the system 20 moves in a direction from the first end 64 toward the second end 66. In the illustrated arrangement, the vent opening 70 opens to the atmosphere; however, in other possible arrangements, the vent opening 70 could communicate with another conduit or component of the system 20 or could be omitted.

Preferably, the passage 62 generally forms the shape of a nozzle having a constricted portion or throat 72, which can define a minimum throat diameter $D_T$. A first portion 74, which can be or include a convergent section in some configurations, is positioned upstream of the throat 72 and a second portion 76, which preferably is or includes a divergent or expansion section, is positioned downstream of the throat 72. Preferably, the vent opening 70 communicates with or opens into the second portion 76 downstream of the throat 72.

In the illustrated arrangement, the first portion 74 defines a first axis $A_F$, the second portion 76 defines a second axis $A_S$ and the vent opening 70 defines a third or vent axis $A_V$. Preferably, the first axis $A_F$ and the second axis $A_S$ are coaxial; however, in some configurations these axes may be non-coaxial. In some configurations, the vent axis $A_V$ is inclined toward the first portion 74 or oriented at an acute angle relative to the first axis $A_F$, such as between about 20 to about 135 degrees, for example and without limitation. Such an arrangement can facilitate desirable fluid flow characteristics in one or both of the inhalation phase or exhalation phase of the breathing cycle. In addition, such an arrangement directs air or gas flow leaving the vent opening 70 away from the patient's face.

Furthermore, the first portion 74 defines a first maximum diameter $D_F$, the second portion 76 defines a second maximum diameter $D_S$ and the vent opening 70 defines a third or vent maximum diameter $D_V$. In some configurations, one or more of the first maximum diameter $D_F$, the second maximum diameter $D_S$ and the vent maximum diameter $D_V$ can be equal or substantially equal to one another. Preferably, one or more of the first maximum diameter $D_F$, the second maximum diameter $D_S$ and the vent maximum diameter $D_V$ is greater than the minimum throat diameter $D_T$. In some configurations, each of the first maximum diameter $D_F$, the second maximum diameter $D_S$ and the vent maximum diameter $D_V$ is greater than the minimum throat diameter $D_T$. Preferably, at least the second maximum diameter $D_S$ is greater than the minimum throat diameter $D_T$ and may be significantly greater, such as about three to about five times as large, for example and without limitation. In some configurations, the diameter $D_S$ is about 3.75 times the diameter $D_T$. In some configurations, the throat diameter $D_T$ can be between about 0.5-2 mm, between about 0.9-1.1 mm, or can be about 1.0 mm.

In some configurations, the passage 62 forms the shape of an asymmetric nozzle in which there exists asymmetry about at least one axis or plane that passes through the passage 62. For example, the convergence angle of the first portion 74 is greater than the expansion angle of the second portion 76. In other words, an axial length or cone length of the convergent section of the first portion 74 is less than an axial length or cone length of the expansion section of the second portion 76. Preferably, the passage 62 forms a relatively smooth curvature along the convergent section of the first portion 74, the throat 72 and the expansion section of the section portion 76. However, in other arrangements, portions of the passage 62 may not form a smooth curvature. In some configurations, the throat may be formed by a restriction plate or plate-like portion having a restricted opening that is smaller than a remainder of the passage. In some such configurations, the restriction plate or plate-like portion can have a surface that extends generally or substantially perpendicular to an axis of the passage. In some configurations, the passage 62 possesses asymmetry between a portion at or near the vent opening 70 (an upper portion in the orientation of the figures) and a portion generally opposite the vent opening 70 (a lower portion in the orientation of the figures). Some or all of the asymmetry may be the result of the presence of the vent opening 70 and the curvature of the passage 62 adjacent the vent opening 70. However, in other some configurations, the passages 62 can possess asymmetry with respect to one or more planes passing through the passage 62 (e.g., lateral or longitudinal) regardless of the presence or absence of the vent opening 70.

Preferably, the passage 62 also defines a curved surface portion 80 extending between the throat 72 and the vent opening 70. The curved surface portion 80 can originate at or near the throat 72 and can extend a substantial distance toward the vent opening 70 or the entire distance to the vent opening 70. Preferably, the curved surface portion 80 extends at least until at or near a point that is radially outside of or beyond the maximum diameter $D_S$ of the second portion 76 or a point on the maximum diameter $D_S$ of the second portion 76 that is angularly aligned with the relevant point or line on the curved surface portion 80. It is believed that the curved surface transition between the throat 72 and the vent opening 70 improves the Coanda effect on the flow of breathing gas within the second portion 76 and results in a more constant CPAP pressure and/or pressure oscillations that better approximate (e.g., amplitude and/or frequency) a bubble CPAP relative to the prior art devices.

In FIG. 2, the curved surface portion 80 is represented by a line; however, preferably the curved surface portion 80 is a three-dimensional surface, which can have curvature about one or more axes (e.g., a lateral axis or axis projecting into and out of the page in FIG. 2 and a lengthwise axis or axis that is generally parallel to the axis $A_S$). In some configurations, the curved surface portion 80 can also have curvature about a vertical axis or axis that lies within the page in FIG. 2 and is substantially perpendicular to the axis $A_S$. For example, portions near or approaching the vent opening 70 can have curvature about the vertical axis. The curved surface portion 80 can be created by lofting between two or more of the throat 72, second end 66, a plane within the second portion 76 defining the second maximum diameter $D_S$ and the vent opening 70. Preferably, the curved surface portion 80 defines a minimum diameter of at least about 0.25 mm to a maximum diameter of preferably about 2 mm. More preferably, the curved surface portion 80 defines a minimum diameter of at least about 1 mm about the lateral axis and, thus, the actual diameter could fall within a range of about 1 mm to about 2 mm, for example. It is believed that such a diameter facilitates the desirable operation of the jet of gas flow within the second portion 76 as is described herein. In some configurations, it is preferable that the vent opening 70 be located close to the throat 72, while still permitting the curved surface portion 80 to have the minimum diameter, as described above.

In operation, the system 20 can be assembled as illustrated in FIG. 1 such that the source of breathing gas 22 is capable of providing a flow of breathing gas to the supply tube(s) 36 and nasal prong(s) 40. Preferably, the flow of breathing gas passes through the positive airway pressure component(s) or connector(s) 50 prior to entering the nasal prong(s) 40. Optionally, the humidification system 24 can be employed to heat and/or humidify the flow of breathing gas. The nasal prong(s) 40 can be inserted into the nare(s) of the infant patient. Preferably, the nasal prong(s) 40 create at least a substantially complete seal or a semi-seal with the nare(s) of the infant. However, the system 20 can be used with non-sealing nasal prong(s) as well. As used herein, non-sealing prongs are not configured to create at least a substantially complete seal with the patient's nares. Semi-sealed prongs refer to situations where the prongs are configured to create at least a substantially complete seal with the nares, but for some reason fail to form the at least substantially complete seal. Such an arrangement allows for more consistent CPAP pressure. The interface member or frame 52 can contact the upper lip (or other portion of the face) of the infant patient and assist in supporting the nasal prong(s) 40 within the nare(s). If necessary or desired, a retention arrangement, such as a head strap, can be used to retain the interface member/frame 52 and/or the nasal prong(s) 40 in place.

A flow of breathing gas can be supplied to the nasal prong(s) 40 by the source 22. The flow of breathing gas moves in a direction from the supply tube(s) 36 to the nasal prong(s) 40, and passes through the positive airway pressure component(s) or connector(s) 50. The movement of the flow of breathing gas through the passage 62 creates a fluid jet (or, simply, a jet) within the second portion 76 as a result of the geometry of the passage 62 and, in particular, the throat 72. By virtue of the Coanda effect, the jet can tend to be attracted to a surface of the second portion 76 of the nozzle. The presence of the vent opening 70, which permits ambient air to enter the second portion 76 of the nozzle and become entrained in the jet, can cause the jet to favor attraction to a surface portion generally opposite the vent opening 70 absent other forces influencing the behavior of the jet. The nozzle geometry, and it is believed particularly the curved surface portion 80, in combination with the breathing action of the patient causes the jet to move between at least two positions within the second portion 76 (e.g., surface portions away from the vent opening 70 and surface portions near the vent opening 70). The movement of the jet creates desirable pressure oscillations within the second portion 76 and the associated nasal prong 40. Preferably, such pressure oscillations produce broad spectrum or distinct tone frequency oscillations, similar to those produced by a bubble CPAP device, but with less expensive and easier to use components 50 that can be implemented or integrated with the patient interface 30.

In some configurations, asymmetry present between a side of the passage 62 containing the vent opening 70 (e.g., upper side) and an opposite side of the passage 62 (e.g., lower side) at least somewhat compensates for the presence of the vent opening 70 to create a balanced, unsteady jet that is relatively neutral in position within the second portion 76 of the passage 62, but readily and, preferably, rapidly changes position (e.g., between a position closer to or attached to the lower surface and a position closer to or attached to the upper surface) in response to static or dynamic pressure changes within the passage 62. For example, changes in pressure within the second portion 76 of the nozzle caused by the breathing action of the patient can create forces tending to influence the behavior of the jet, which can include causing or facilitating movement of the jet between the surface portion opposite the vent opening 70 and the surface portion on the same side as the vent opening 70 or other surface portions of the second portion 76 of the nozzle. It is believed that the readily-movable jet creates desirable pressure oscillations within the second portion 76 and the associated nasal prong 40 that better mimic those produced by a bubble CPAP device in comparison to the existing prior art nozzle-type CPAP devices.

In general, during inhalation by the patient, ambient air can enter the passage 62 through the vent opening 70 and join the flow of breathing gas provided by the source 22. Such an arrangement reduces the pressure drop that might otherwise occur within the second portion 76 and/or nasal prongs 40. Pressure oscillations may occur during inhalation, which are beneficial to the infant patient. The pressure oscillations can be beneficial in alveolar recruitment of the lungs (i.e., reopening of collapsed alveoli). During exhalation by the patient, the exhalation flow occurs in a direction opposite flow of breathing gas supplied by the source 22, moving from the nasal prongs 40 to the second portion 76 of the passage 62 and exiting the vent opening 70. The flow of breathing gas supplied by the source 22 continues during exhalation and ensures that a positive airway pressure is maintained. As described above, the exhalation by the patient interacts with the jet within the second portion 76 of the passage 62 to create pressure oscillations that are beneficial to the infant patient. Pressure oscillations can be desirable during exhalation, inhalation or both.

FIGS. 3-11 illustrate another configuration of a positive airway pressure component 50, which is similar in many respects to the positive airway pressure component 50 of FIGS. 1 and 2. Accordingly, the same reference numbers are used to indicate the same or similar components or features. The description of FIGS. 3-11 is directed primarily toward the differences relative to the component 50 of FIGS. 1 and 2. Therefore, any portions or features not described in detail can be assumed to be similar to the corresponding portion or feature of the component of FIGS. 1 and 2. For the sake of clarity, FIGS. 3-11 illustrate the shape of the passage 62, without showing the body 60 of the component 50 that forms the passage 62. In some configurations, the component 50 of FIGS. 3-11 is a connector that is interposed between a supply tube 36 and a nasal prong 40. However, in other configurations, the component 50 or passage 62 can be integrated within a patient interface or other portion of a breathing assistance system.

Unlike the passage 62 of the connector 50 of FIGS. 1 and 2, the first portion 74 of the illustrated passage 62 of FIGS. 3-11 does not include a convergent section. Rather, the first portion 74 is generally or substantially consistent in cross-sectional shape and/or size. In the illustrated arrangement, the first portion 74 defines a substantially circular cross-sectional shape; however, other suitable shapes may also be used. Unlike the passage 62 of FIGS. 1 and 2, the throat 72 can be similar to the first portion 74 in cross-sectional size and/or shape. In some configurations, the supply tube 36 (FIG. 1) can have a cross-sectional size and/or shape that is different than the cross-sectional size and/or shape of the first portion 74. For example, the supply tube 36 can have a larger cross-sectional size than the first portion 74 to reduce the energy required to provide a desired flow rate of the breathing gas. In such an arrangement, the first portion 74 can provide a similar function to the throat 72.

In the illustrated configuration, the vent axis $A_V$ of the vent opening 70 is generally or substantially perpendicular to one or both of the first axis $A_F$ and the second axis A. However, the passage 62 can define a vent portion 90 having a first or upstream surface 92 and a second or downstream surface 94 relative to the flow of breathing gas and when viewed from the side or a longitudinal cross-section. At least one, and preferably each, of the first surface 92 and the second surface defines at least a portion that is canted or angled toward the first portion 72 of the passage 62. In the illustrated configuration, the first surface 92 generally is canted toward the first portion 72 to a greater extent than the second surface 94. In addition, an upper portion of the second surface 94 nearest the vent opening 70 can be generally or substantially perpendicular to one or both of the first axis $A_F$ and the second axis $A_S$. A central axis $A_{V2}$ of the vent portion 90 can be defined as a line extending along the geometric center of the vent portion 90 and can be angled relative to one or both of the first axis $A_F$ and the second axis A. In the illustrated arrangement, the central axis $A_{V2}$ is a curved lined. However, in other arrangements, depending on the geometry of the vent portion 90, the central axis $A_{V2}$ can be straight. In the illustrated arrangement, the central axis $A_{V2}$ generally defines an acute angle with each of the first axis $A_F$ and the second axis $A_S$. In some alternative configurations, the vent opening 70 can be non-parallel, or the vent axis $A_V$ can be non-perpendicular, to the first axis $A_F$ or second axis $A_S$.

Preferably, similar to the passage 62 of FIGS. 1 and 2, the passage 62 of FIGS. 3-11 is asymmetric between a lower portion (opposite the vent portion 90) and an upper portion (on the same side or containing the vent portion 90) and includes the curved surface portion 80 extending between the first portion 74 and the vent portion 90 or vent opening 70. The curved surface portion 80 can have a single radius (can be a constant-radius curve) or multiple radii about a single point (can be a variable-radius curve) or about multiple points. As described above, the curved surface portion 80 can be formed by a loft between two or more profiles defined by the passage 62, such as two or more profiles defined by the throat 72, the second portion 76 (e.g., a plane within the second portion 76 defining the second maximum diameter $D_S$), the vent portion 90 and the vent opening 70. Preferably, a length of the curved surface portion 80 in a longitudinal or flow direction is significant relative to an overall length of the passage 62 and/or the diameter $D_T$ of the throat 72. In other words, preferably, the curved surface portion 80 is more than simply a small chamfer between the throat 72 and the vent portion 90. In some configurations, the length of the curved surface portion 80 is equal to or greater than the diameter $D_T$ of the throat 72. In some configurations, the length of the curved surface portion 80 can be about two, three or four times greater than the diameter $D_T$ of the throat 72, including any specific value or smaller range within this range of values. In some configurations, the length of the curved surface portion 80 is equal to or greater than the diameter $D_S$ of the second portion 76 and/or the diameter $D_V$ of the vent opening 70. In other configurations, the length of the curved surface portion 80 is equal to or greater than a substantial portion (e.g., at least about 50, 75 or 90% or any value or range within these ranges) of the diameter $D_T$ of the diameter $D_S$ of the second portion 76 and/or the diameter $D_V$ of the vent opening 70. It is believed that such a curved surface portion 80 contributes to the desirable pressure oscillations and/or steady pressure characteristics of the present positive pressure components 50. In addition, preferably, the curved surface portion 80 defines a minimum diameter of at least about 0.25 mm or, more preferably, at least about 1 mm up to a maximum diameter of about 2 mm about the lateral axis, including any value or sub-range within either of these ranges, similar to the configuration of FIGS. 1 and 2, as described above.

Figure 4:
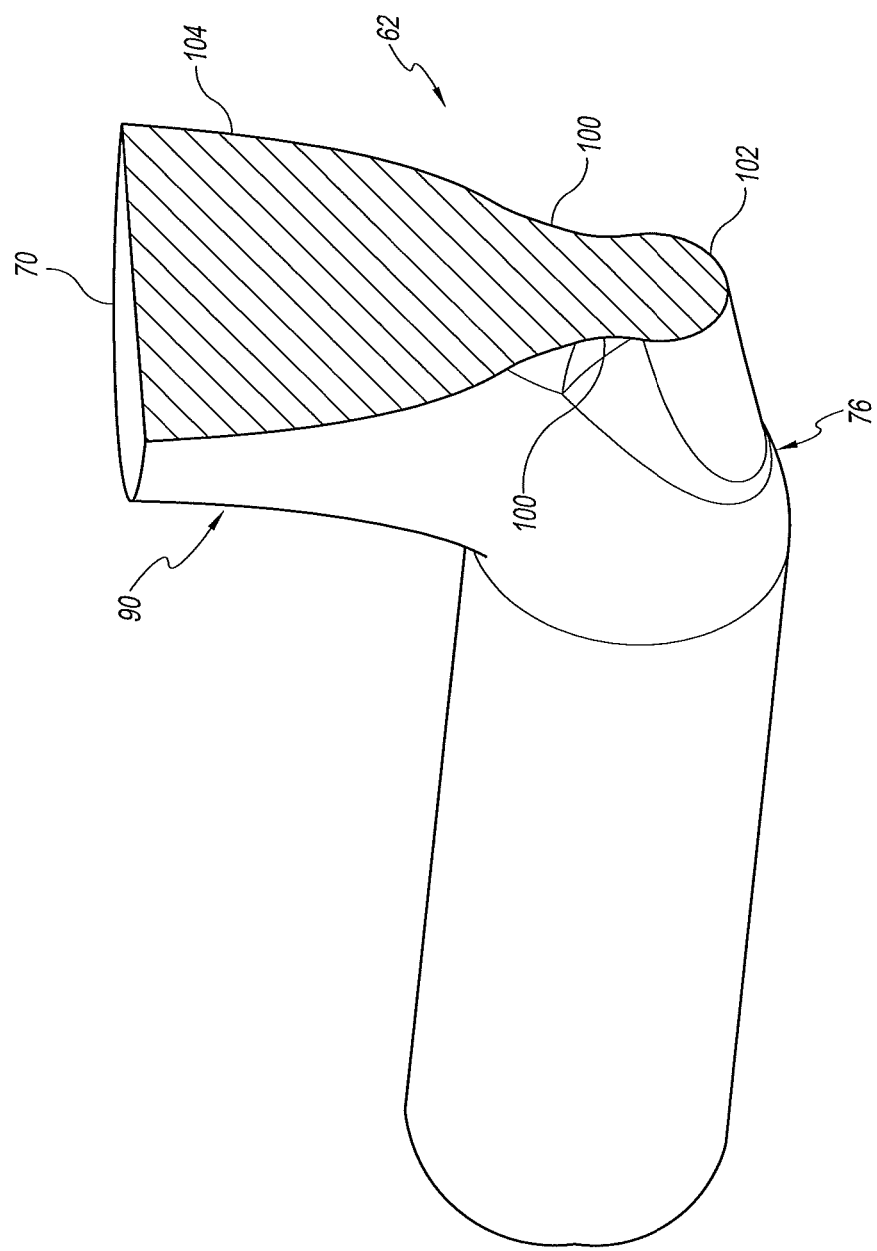
FIG. 4 is perspective, sectional view of the passage of FIG. 3.

With reference to FIG. 4, at least some configurations of the passage 62 includes a "pinched" geometry transition between a portion of the vent portion 90 or vent opening 70 and a portion of the second portion 76. That is, a vertical plane (or plane that is substantially perpendicular to one or both of the first axis $A_F$ and second axis $A_S$) can extend through the passage 62 within the vent portion 90 such that, within the cut plane, the passage 62 defines a generally hourglass shape having a pair of opposed transition surface portions or concave surface portions 100 positioned vertically between a bottom section 102 of the second portion 76 and a top section 104 of the vent portion 90. That is, preferably, at least a portion of the opposed transition surface portions 100 are curved surfaces defined by one or more radii about one or more points that lie outside of the passage 62 or that is positioned on an opposite side of the curved surface from a central, bisecting plane of the passage 62.

Figure 3:
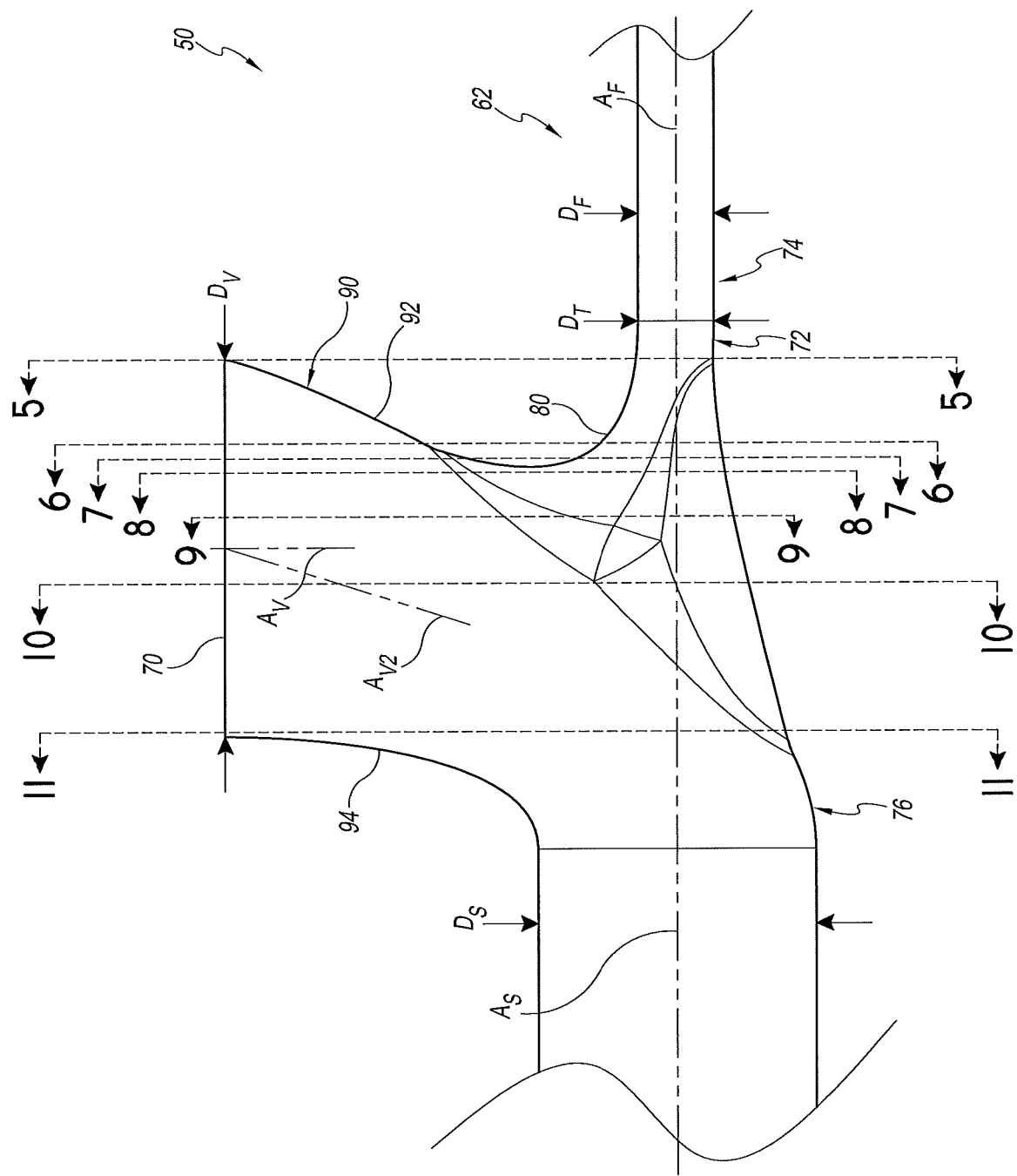
FIG. 3 is a side view of a modified version of the passage of FIG. 2.
Figure 5:
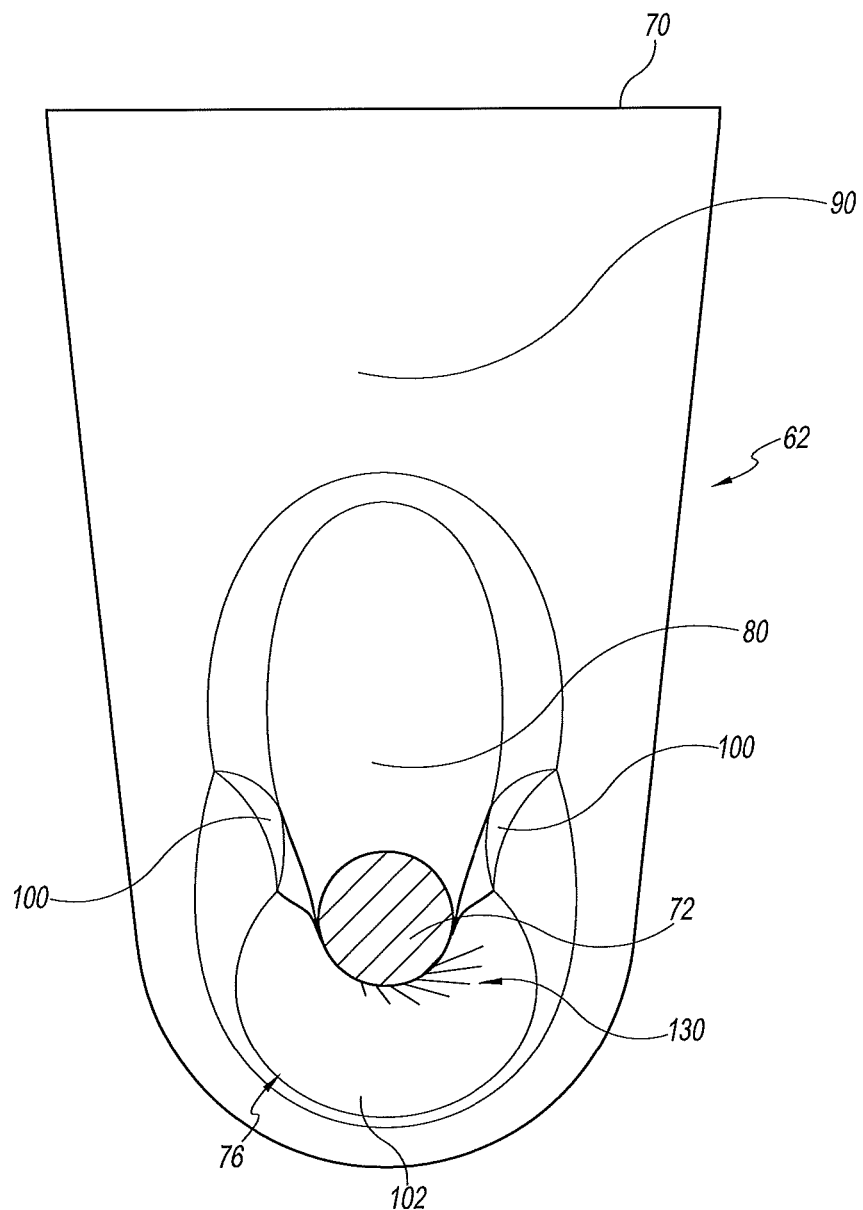
FIG. 5 is a sectional view of the passage of FIG. 3 taken along the line 5-5 of FIG. 3.

FIGS. 5-11 illustrate the passage 62 of FIGS. 3 and 4 in sectional views taken along the lines indicated in FIG. 3 and viewed in a downstream direction relative to the flow of breathing gas. FIG. 5 is a sectional view taken through a point at or near the throat 72. As illustrated, the throat 72 can be substantially circular in cross-sectional shape. The curved surface portion 80 generally extends downstream and upwardly from the throat 72 toward the vent portion 90. The bottom section 102 of the second portion 76 generally extends downstream and downwardly from the throat 72. The concave curved portions 100 generally extend between the bottom section 102, the curved surface portion 80 and the vent portion 90.

Figure 6:
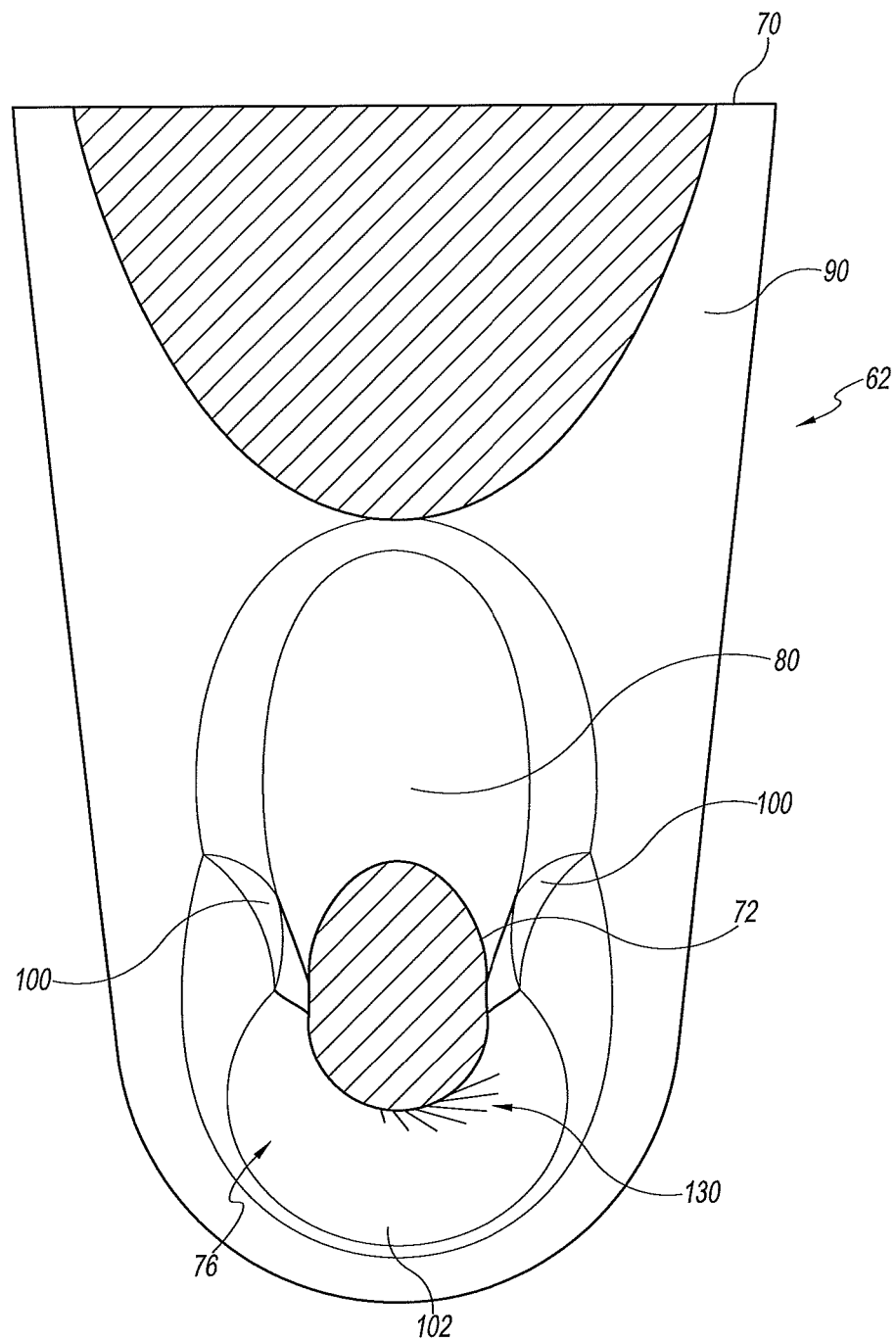
FIG. 6 is a sectional view of the passage of FIG. 3 taken along the line 6-6 of FIG. 3.

With reference to FIG. 6, the sectional view is taken through an intermediate location of the curved surface portion 80 and illustrates that the second portion 76 of the passage 62 is generally oval in shape within the cut plane. In the illustrated configuration, the upper edge of the second portion 76 of the passage 62 extended upwardly a greater distance than a distance that the bottom edge extended downwardly relative to the passage 62 within the cut plane of FIG. 5. Similarly, with reference to FIG. 7, the upper edge of the second portion 76 of the passage 62 again extended upwardly a greater distance than a distance that the bottom edge extended downwardly relative to the second portion 76 of the passage 62 within the cut plane of FIG. 6. In addition, the upper edge of the second portion 76 of the passage 62 defines a more elongated or parabolic shape relative to the shape of the second portion 76 of the passage 62 of FIG. 6. In each of FIGS. 6 and 7, the passage 62 grew in size in a vertical direction to a greater extent than in a lateral or horizontal direction relative to one another and to the passage 62 within the cut plane of FIG. 5, thus illustrating the "pinched" geometry of the passage 62.

Figure 7:
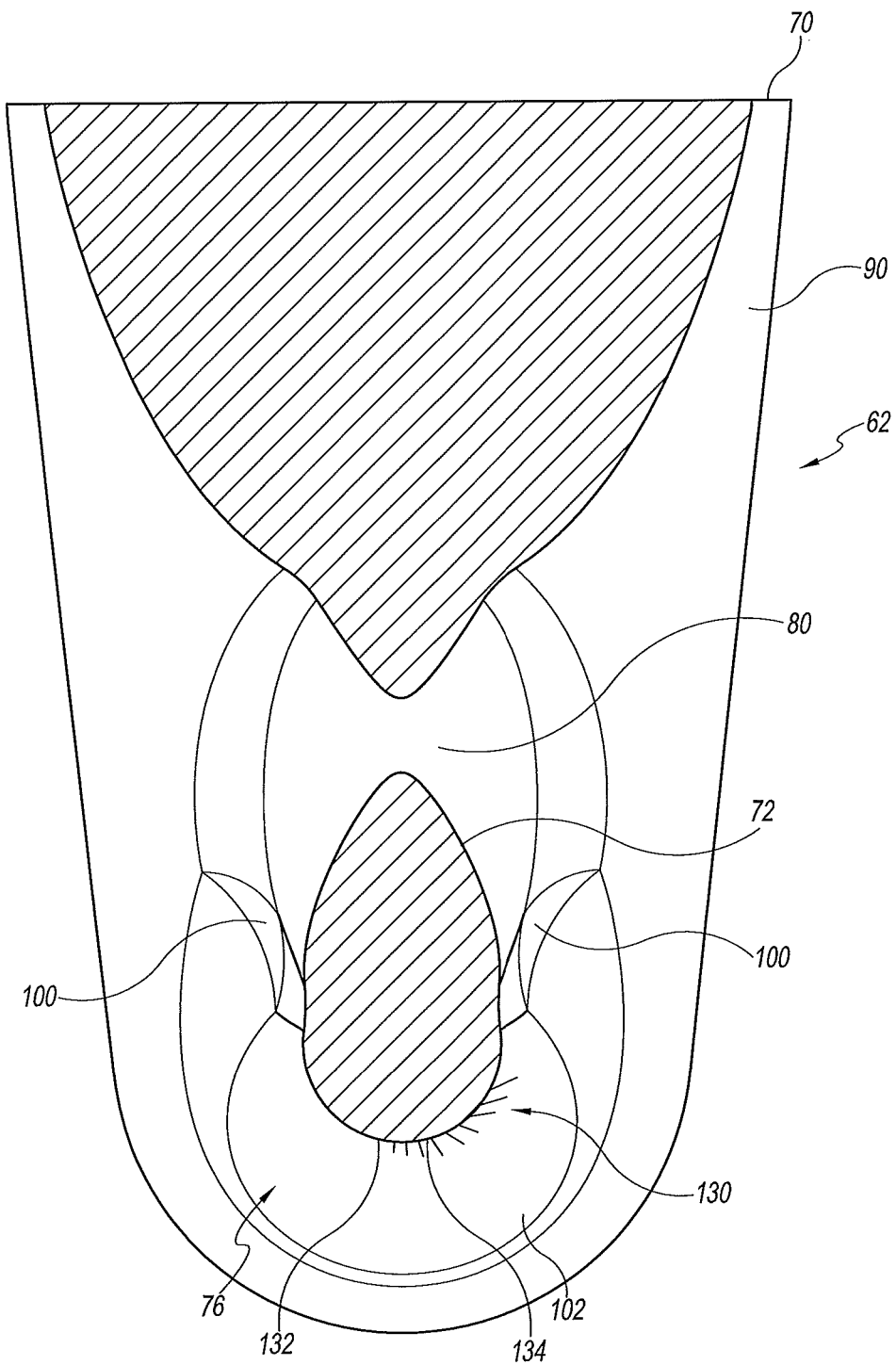
FIG. 7 is a sectional view of the passage of FIG. 3 taken along the line 7-7 of FIG. 3.
Figure 8:
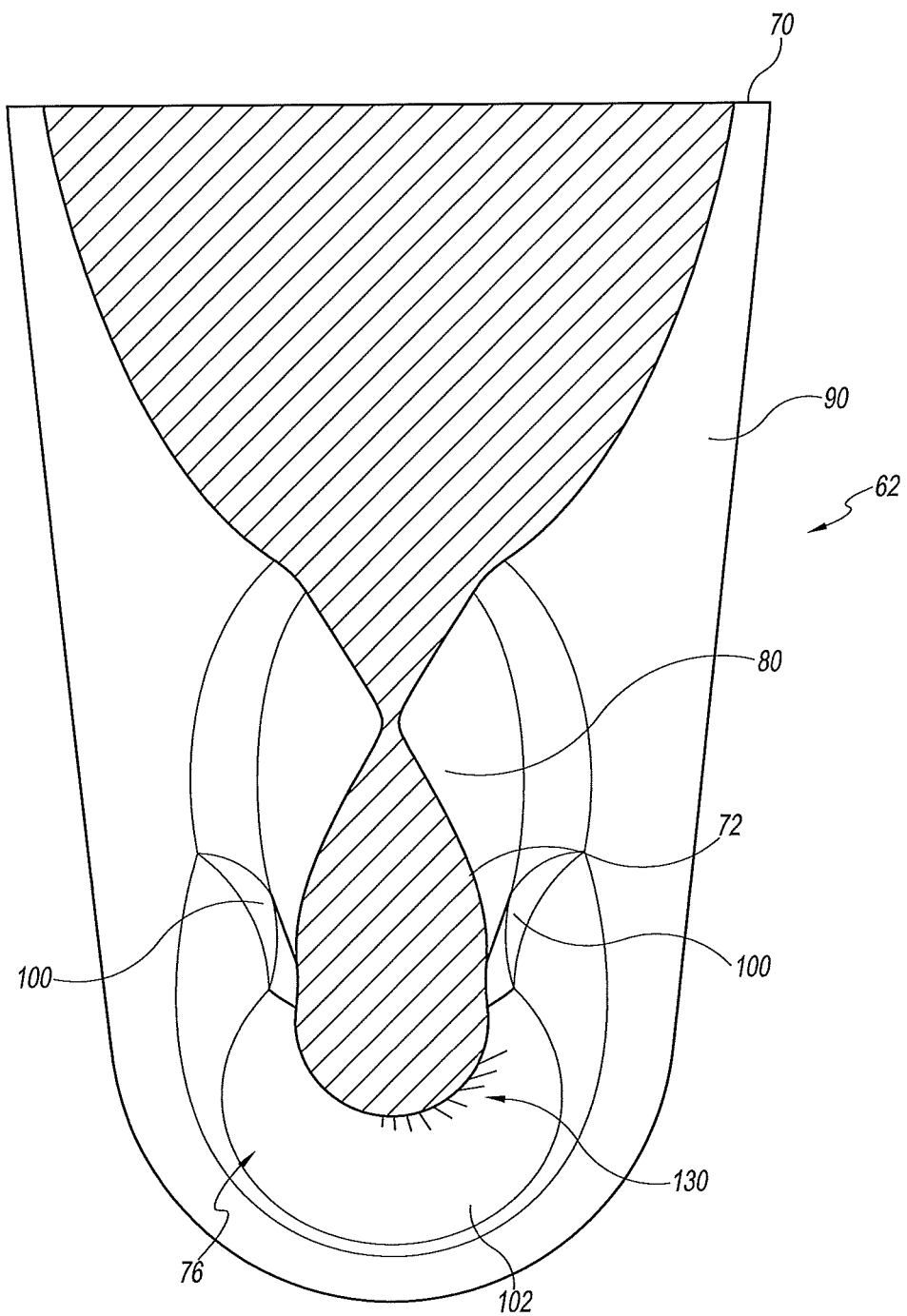
FIG. 8 is a sectional view of the passage of FIG. 3 taken along the line 8-8 of FIG. 3.

FIG. 8 is a sectional view taken just downstream of a location at which the flow can communicate with the vent portion 90. Again, the upper edge of the second portion 76 of the second portion 76 of the passage 62 extended upwardly a greater distance than a distance that the bottom edge extended downwardly relative to the second portion 76 of the passage 62 within the cut plane of FIG. 7. In addition, the passage 62 grew in size in a vertical direction to a greater extent than in a lateral or horizontal direction relative to the passage 62 within the cut plane of FIG. 7. In addition, as illustrated by FIGS. 6, 7 and 8, the upper edge of the second portion 76 extends upwardly a greater distance in each view than a distance that a lower edge of the vent portion 90/upper portion of the curved surface portion 80 extends downwardly. In other words, the upper edge of the second portion 76 extends upwardly a greater rate than the lower edge of the vent portion 90/upper portion of the curved surface portion 80 extends downwardly when moving in a downstream direction along the axes $A_F$, $A_S$ of the passage 62.

Figure 9:
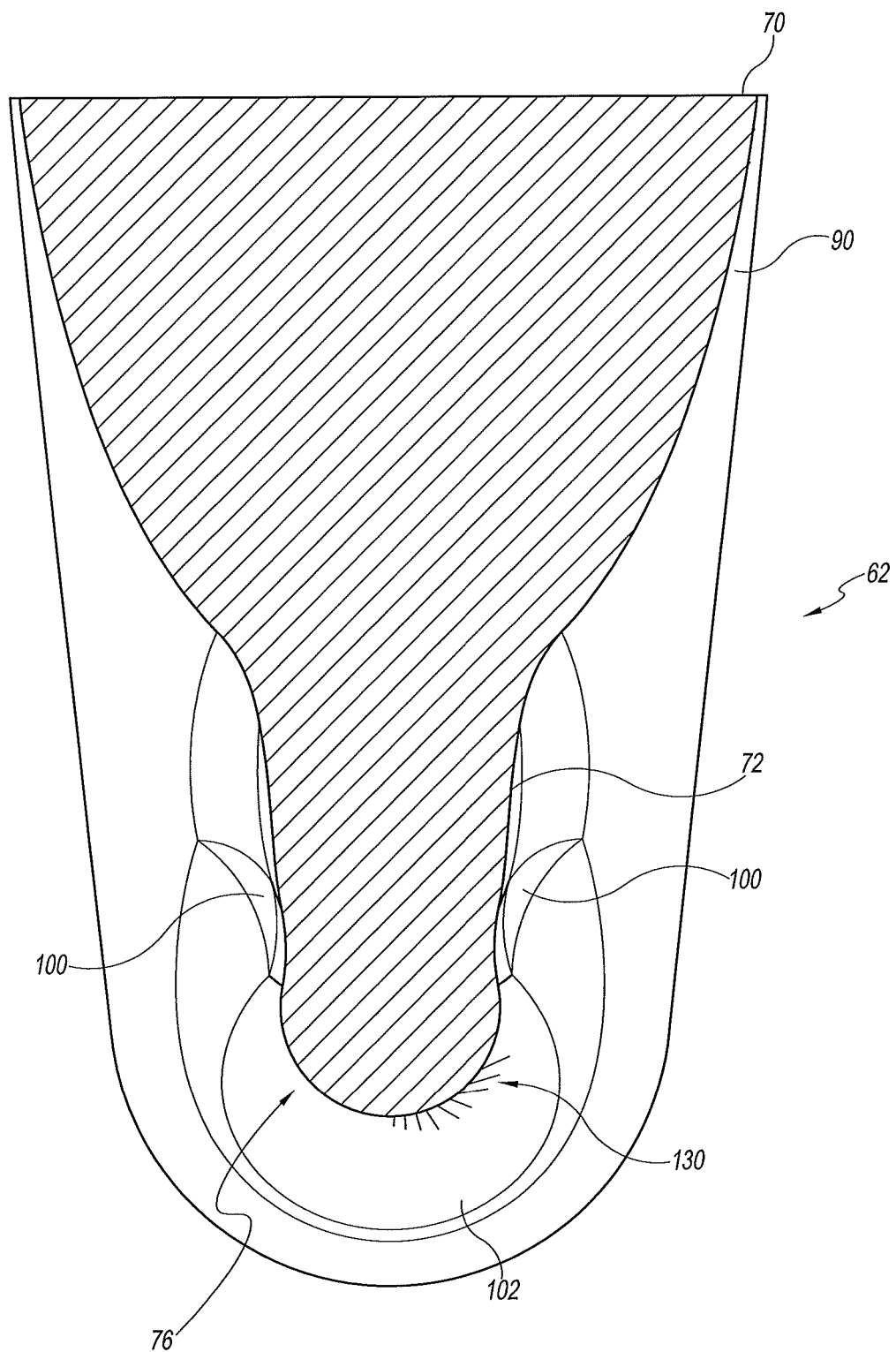
FIG. 9 is a sectional view of the passage of FIG. 3 taken along the line 9-9 of FIG. 3.
Figure 10:
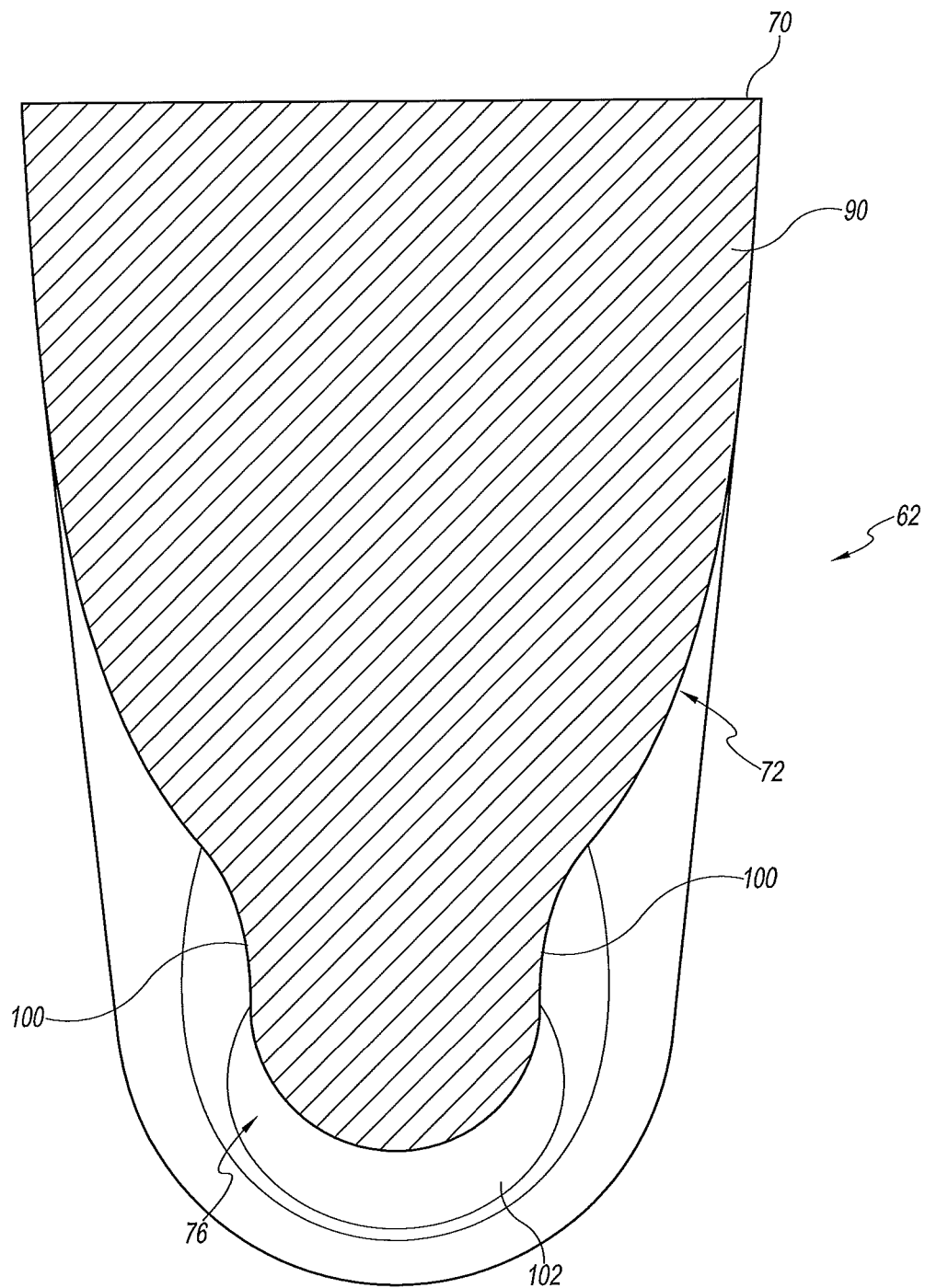
FIG. 10 is a sectional view of the passage of FIG. 3 taken along the line 10-10 of FIG. 3.

FIGS. 9 and 10 illustrate two additional sectional views taken downstream of FIGS. 5-8, with the cut plane of FIG. 10 being positioned downstream of the cut plane of FIG. 9. FIGS. 9 and 10 illustrate the transition surface portions 100 positioned vertically between a bottom section 102 of the second portion 76 and a top section 104 of the vent portion 90. In FIG. 9, the transition surface portions 100 define mildly curved or substantially straight surfaces extending generally in a vertical direction. In FIG. 10, the transition surface portions 100 have a greater curvature relative to the transition surface portions 100 of FIG. 9.

Figure 11:
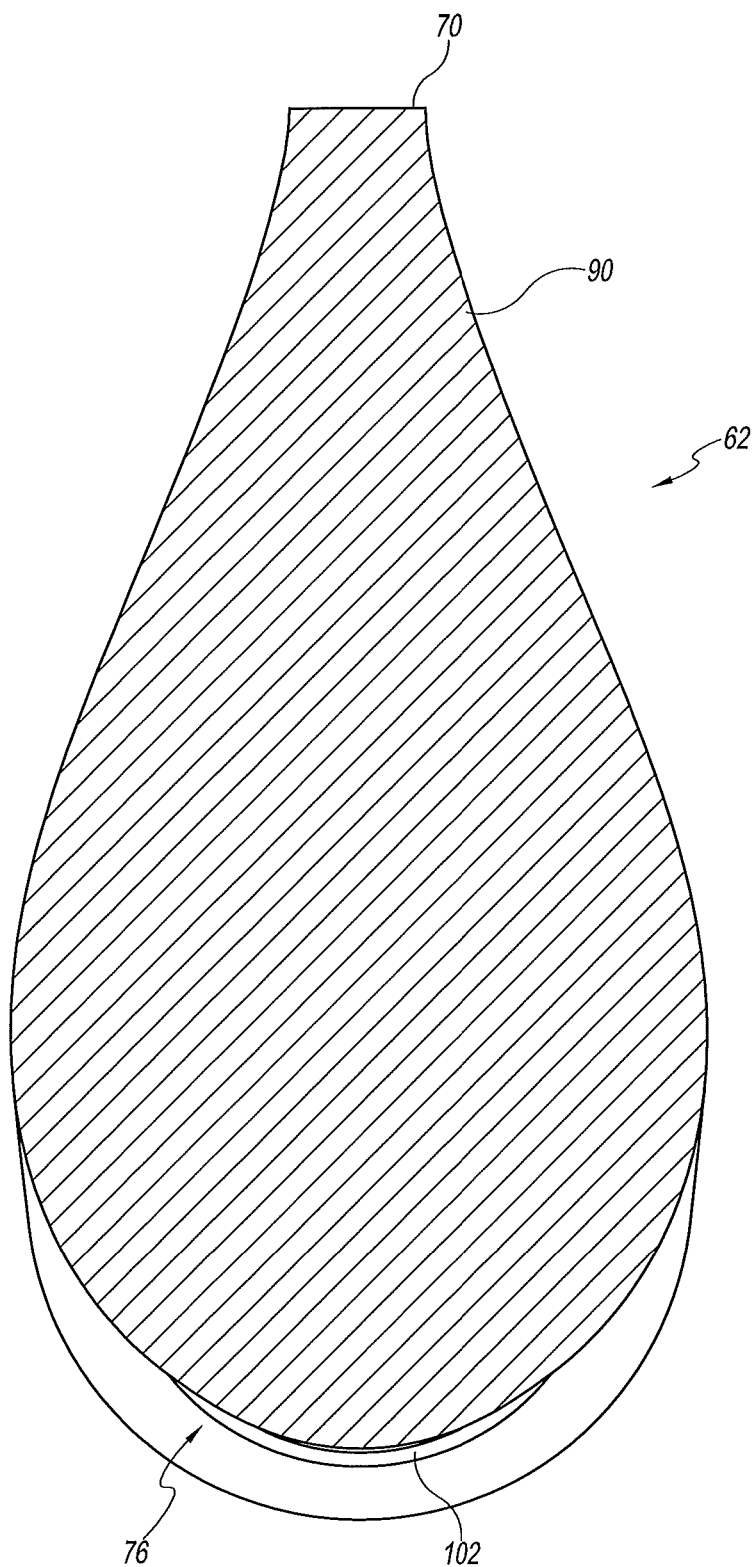
FIG. 11 is a sectional view of the passage of FIG. 3 taken along the line 11-11 of FIG. 3.

FIG. 11 is a sectional view taken near a downstream end of the vent portion 90 and, more particularly, at or near a downstream end of the vent opening 70. FIG. 11 illustrates that the passage 62 is generally a teardrop shape within the cut plane near the downstream end of the vent portion 90. In addition, FIG. 11 illustrates that the lower edge of the passage 62 within the cut plane (and at or near the downstream end of the vent opening 70) is spaced above the lowermost point of the passage 62 that is downstream of the cut plane. That is, the lower edge of the passage 62 continues to extend downwardly or away from the second axis $A_S$ downstream of the cut plane of FIG. 11.

In some configurations, at least the bottom section 102 of the second portion 76 is twisted or torsionally-rotated about the second axis $A_S$ to define a twisted portion 130. As illustrated in FIGS. 5-10, in the illustrated configuration, at least the bottom section 102 of the second portion 76 is twisted in a clockwise direction when viewed in a downstream direction. However, in other arrangements, the twisting can be in the counter-clockwise direction. In addition, a portion greater than the bottom section 102 of the second portion 76 can be twisted, such as up to an entire circumferential portion, for example. The twisted portion 130 can define any suitable twist angle, such as between about 45 degrees and about 90 degrees, or any value or sub-range within this range of values. In some embodiments, the expiratory or vent portion 90 and/or the first portion 74 can comprise a similar twisted portion in addition to or in the alternative of the twisted portion 130. With specific reference to FIGS. 6-8, while the illustrated embodiments of the twisted portion 130 define a smooth surface, it is also contemplated that the twisted portion 130 can define a non-smooth surface. For example, the twisted portion 130 can define a plurality of folds or pleats, which create ridges, high points or portions, or radially-inward points or portions and valleys, low points or portions, or radially-outward points or portions. The terms "high" and "low" are used in the context of the twisted portion 130 being positioned partially or entirely within the bottom section 102 in the orientation shown in FIGS. 5-11 such that radially-inward points are relatively "higher" and radially-outward points are relatively "lower." Preferably, the twisted portion 130 extends a substantial length along the second axis AS, such as at least about ¼ of a length of the second portion 76 or at least about ½ of the length of the second portion 76, including any value or sub-range of values within those ranges. In some configurations, the twisted portion 130 extends about ½ the length of the second portion 76 or to at or downstream of about a mid-point of the vent opening 70.

Figure 12:
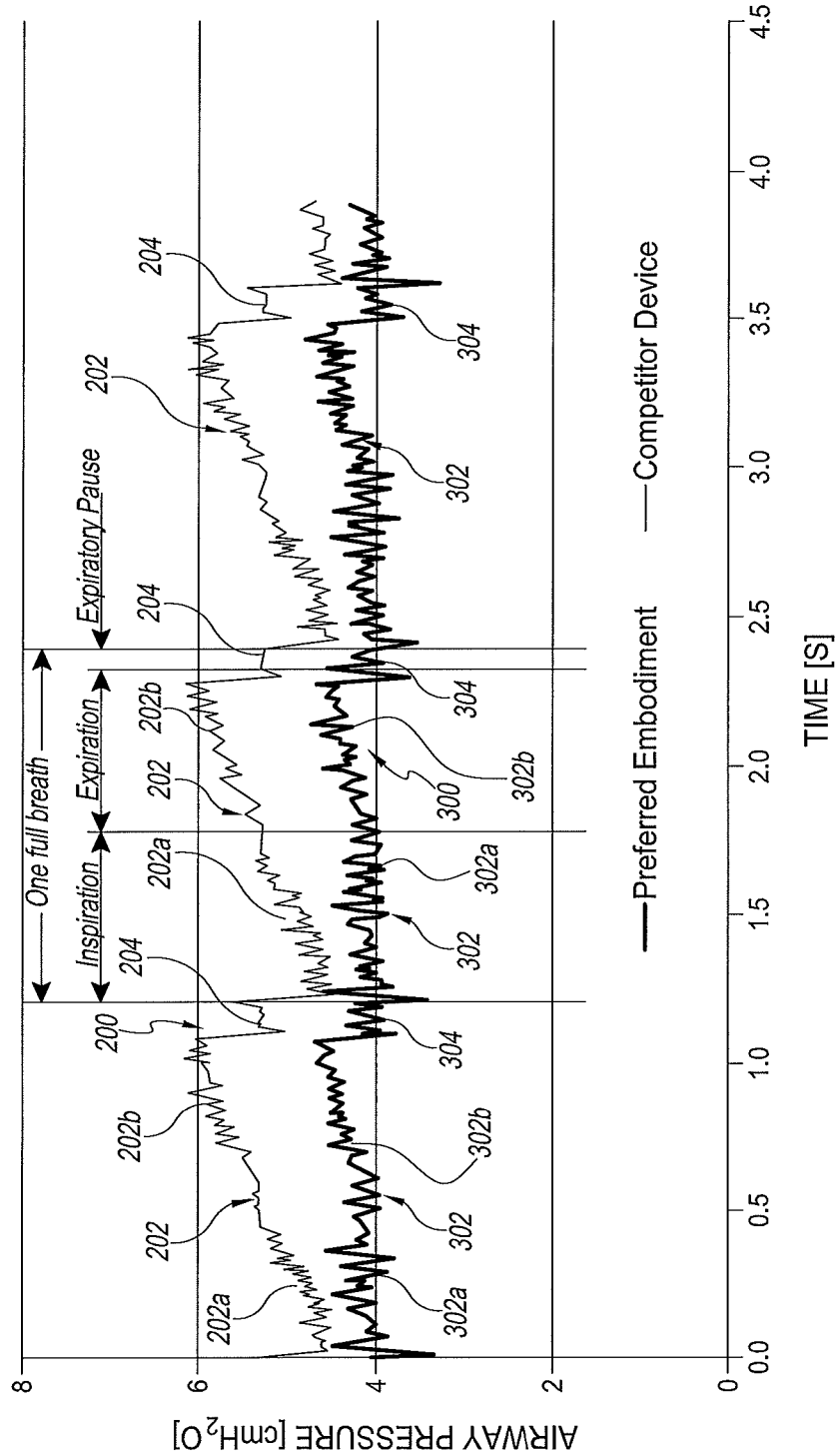
FIG. 12 is a graph of airway pressure over time comparing a device utilizing a pair of passages similar to the passage of FIGS. 3-11 and a prior art device on a test apparatus having simplified nostrils.

FIG. 12 is a graph of time (in seconds) on the x-axis versus airway pressure (in centimeters of water) on the y-axis comparing a non-limiting embodiment of the present passage 62 (similar to the passage illustrated and described with reference to FIGS. 3-11) to a competitive device currently on the market. The graph of FIG. 12 is based on a pair of components 50 having passages 62 similar to those of FIGS. 3-11 communicating with nasal prongs inserted into simplified test "nostrils" with a substantially perfect seal. Similarly, the competitive device was mounted on simplified test "nostrils" with a substantially perfect seal.

Line 200 represents the results of the competitive device over three breathing cycles. The middle breathing cycle is labeled in FIG. 12; however, the first and last breathing cycles have similar phases or portions. The first portions 202a of the upwardly sloping line segments 202 represent an inspiration or inhalation phase of the breathing cycle and the second portions 202b of the upwardly sloping line segments 202 represent an expiration or exhalation phase of the breathing cycle. The upwardly sloping line segments 202 begin below 5 cm/$H_2O$ (at or near about 4.5 cm/$H_2O$) and rise to at or near about 6 cm/$H_2O$ over a duration of about 1 second. The expiratory pause portions of the breathing cycles are represented by the generally horizontal or downwardly sloping line segments 204. The breathing cycles are substantially similar to one another. In general, it is desirable for the pressure to remain relatively constant during the breathing cycle. The difference between the maximum pressure and the minimum pressure over the breathing cycle is related to the work of breathing for the infant patient. In general, a lower work of breathing is desirable. In addition, the line segments 202a, 202b and/or 204 are not smooth or straight, but vary or oscillate about a generally upwardly or downwardly sloping average line. These variations or oscillations in pressure are desirable in the treatment of the infant patient and can be similar to pressure oscillations provided by a bubble CPAP machine or bubbler. In general, larger pressure oscillations are desirable.

Line 300 represents the results of the non-limiting embodiment of the present passage 62 (similar to the passage illustrated and described with reference to FIGS. 3-11) over three breathing cycles. Similar to the line 200, the first portions 302a and second portions 302b of the upwardly sloping line segments 302 represent an inspiration (or inhalation) and expiration (or exhalation) phase, respectively, of the breathing cycle and the generally horizontal or downwardly sloping line segments 304 represent an expiratory pause portion of the breathing cycle. The upwardly sloping line segments 302 begin at about 4 cm/$H_2O$ and rise to at or near about 4.5 cm/$H_2O$ over a duration of about 1 second. Advantageously, the pressure of curve 300 is substantially more constant (i.e., lower total variation between the minimum pressure and the maximum pressure) than the curve 200. Thus, the non-limiting embodiment of the present passage 62 (similar to the passage illustrated and described with reference to FIGS. 3-11) provides a more constant pressure and lower work of breathing compared to the competitive device. In addition, in general, the pressure oscillations of the line 300 have greater amplitude than the oscillations of the line 200. The present inventors believe that the unique geometry of the passages 62 described herein are at least partially or largely responsible for the improved performance illustrated by line 300 in FIG. 12.

The geometry of the passage 62 can be modified (e.g., by changing the curved surface portion 80, the vent portion 90 or any aspect of the nozzle geometry) to achieve different performance criteria. For example, for some applications or treatments, it is desirable to select the geometry of the passage 62 to provide an average pressure of between about 3-8 or about 5-7 cm of $H_2O$ Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

The invention claimed is:

1. An infant patient nasal interface for use with a respiratory therapy system that delivers a flow of breathing gas, the interface comprising:
   at least one nasal prong configured to be inserted within a nare of an infant patient,
   a conduit portion upstream from the nasal prong relative to the flow of breathing gas and defining an interior passage in a nozzle shape having a throat, a first portion upstream of the throat and a second portion downstream of the throat, the interior passage having a vent opening within the second portion,
   wherein the interior passage defines a continuously curved, non-movable surface extending between the throat and the vent opening.

2. The infant patient nasal interface of claim 1, wherein the vent opening defines a vent opening axis that forms an acute angle with a first axis defined by the first portion.

3. The infant patient nasal interface of claim 1, wherein the second portion is divergent.

4. The infant patient nasal interface of claim 3, wherein the first portion is convergent.

5. The infant patient nasal interface of claim 3, wherein the first portion defines a substantially constant cross-sectional size and shape.

6. The infant patient nasal interface of claim 5, wherein the cross-sectional size and shape of the first portion is substantially identical to a cross-sectional size and shape of the throat.

7. The infant patient nasal interface of claim 1, wherein the first portion defines a first axis and the second portion defines a second axis, wherein the first axis and the second axis are coaxial.

8. The infant patient nasal interface of claim 1, wherein the interior passage further comprises a pair of opposed transition surface portions between a bottom section of the second portion and a vent portion that defines the vent opening, wherein the transition surface portions create a generally smooth transition between the bottom section of the second portion and the vent portion and are devoid of sharp corners or edges.

9. The infant patient nasal interface of claim 8, wherein the transition portions are either linear or of a concave curvature.

10. The infant patient nasal interface of claim 1, wherein the second portion defines a second axis and at least a bottom section of the second portion is twisted about the second axis.

11. An infant patient nasal respiratory therapy system, comprising:
   a pair of nasal prongs;
   a first supply tube and a second supply tube, each of which supplies a flow of breathing gas to a respective one of the pair of nasal prongs,
   a pair of connectors that each connect one of the first and second supply tubes to one of the nasal prongs, each connector defining an interior passage in a nozzle shape having a throat, a first portion between the supply tube and the throat and a second portion between the throat and the nasal prong, the interior passage having a vent opening within the second portion, wherein the interior passage defines a continuously curved, convex surface extending the entire distance between the throat and the vent opening.

12. The system of claim 11, wherein the pair of nasal prongs, the first and second supply tubes and the pair of connectors are separate from one another.

13. The system of claim 12, further comprising a frame portion that supports at least one of the pair of nasal prongs and the pair of connectors.

14. The system of claim 11, wherein the vent opening defines a vent opening axis that forms an acute angle with a first axis defined by the first portion.

15. The system of claim 11, wherein the second portion is divergent.

16. The system of claim 15, wherein the first portion is convergent.

17. The system of claim 15, wherein the first portion defines a substantially constant cross-sectional size and shape.

18. The system of claim 17, wherein the cross-sectional size and shape of the first portion is substantially identical to a cross-sectional size and shape of the throat.

19. The system of claim 11, wherein the first portion defines a first axis and the second portion defines a second axis, wherein the first axis and the second axis are coaxial.

20. The system of claim 11 further comprising a flow generator that generates the flow of breathing gas.

21. The system of claim 20, further comprising a humidifier downstream of the flow generator that humidifies the flow of breathing gas supplied to the first and second supply tubes.

22. The system of claim 11, wherein the second portion defines a second axis and at least a bottom section of the second portion is twisted about the second axis.

23. The system of claim 11, wherein the pair of nasal prongs are configured to create at least a substantially complete seal with a patient's nares.

* * * * *